United States Patent [19]

DiGiovanni et al.

[11] Patent Number: 5,395,382
[45] Date of Patent: Mar. 7, 1995

[54] DEVICE FOR TYING INTRACORPOREAL KNOT

[75] Inventors: John DiGiovanni, Woodbridge; Gene Kammerer, East Brunswick, both of N.J.

[73] Assignee: Ethicon, Inc., Somerville, N.J.

[21] Appl. No.: 141,449

[22] Filed: Oct. 22, 1993

[51] Int. Cl.⁶ ............................................. A61B 17/04
[52] U.S. Cl. .................................. 606/148; 606/139
[58] Field of Search .................. 606/1, 139, 144, 145, 606/148, 113

[56] References Cited

U.S. PATENT DOCUMENTS

| | | | |
|---|---|---|---|
| 2,012,776 | 8/1935 | Roeder | 606/144 |
| 4,177,813 | 12/1979 | Miller et al. | 606/139 |
| 5,129,912 | 7/1992 | Noda et al. | 606/139 |
| 5,144,961 | 9/1992 | Chen et al. | 606/148 |
| 5,152,769 | 10/1992 | Baber | 606/139 |
| 5,234,445 | 8/1993 | Walker et al. | 606/139 |
| 5,292,327 | 3/1994 | Dodd et al. | 606/139 |

*Primary Examiner*—Stephen C. Pellegrino
*Assistant Examiner*—Gary Jackson
*Attorney, Agent, or Firm*—Emil Richard Skula

[57] ABSTRACT

An intracorporeal knot tying device. The knot tying device comprises a cannula tube having a proximal end and a distal end and passage therethrough. A suture is movably mounted within the tubular passage. A needle is mounted to the distal end of the suture. The cannula has in its distal end a slit or a distally extending arm for retaining the suture and maneuvering the suture while tying an intracorporeal knot.

15 Claims, 8 Drawing Sheets

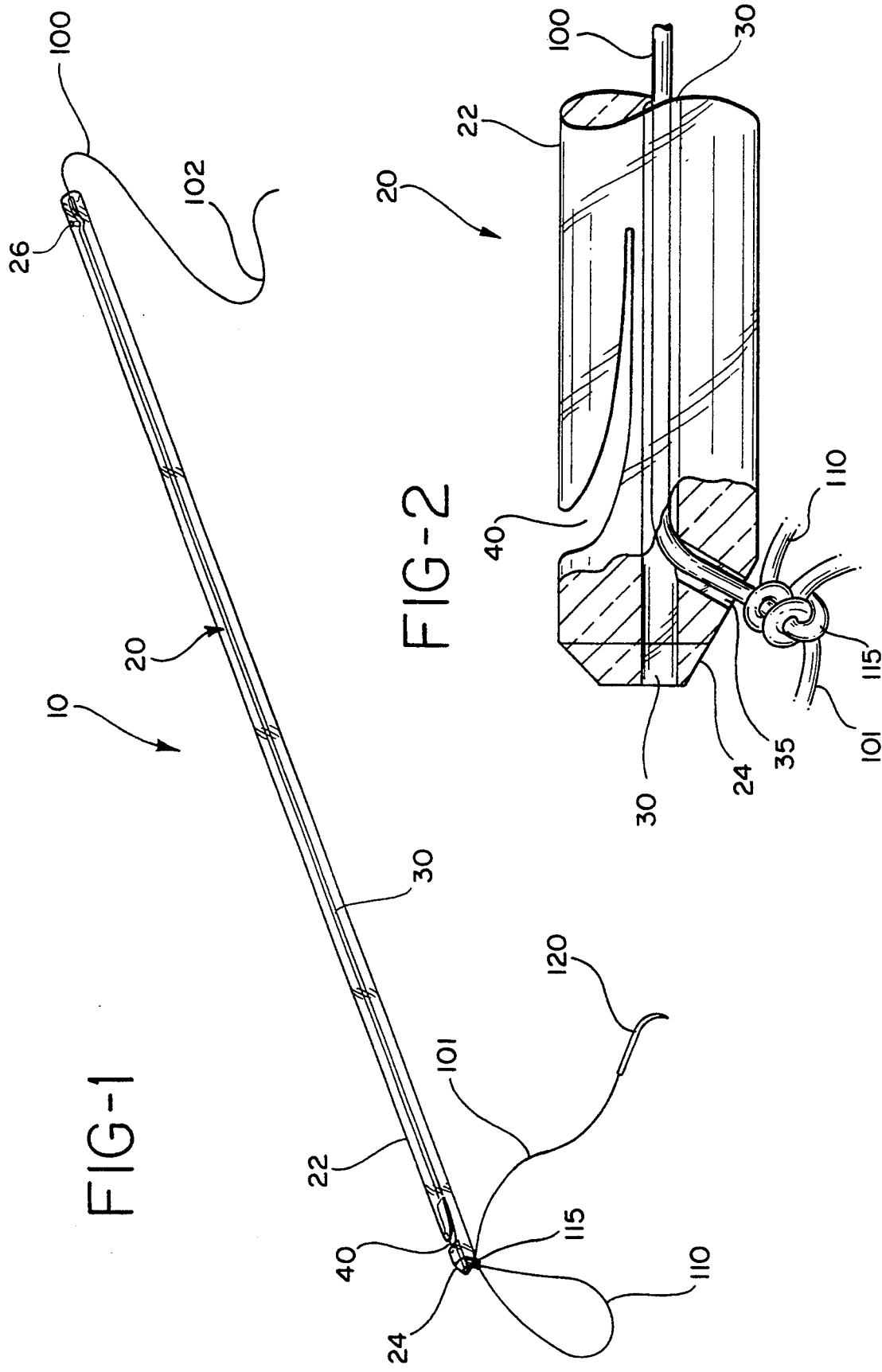

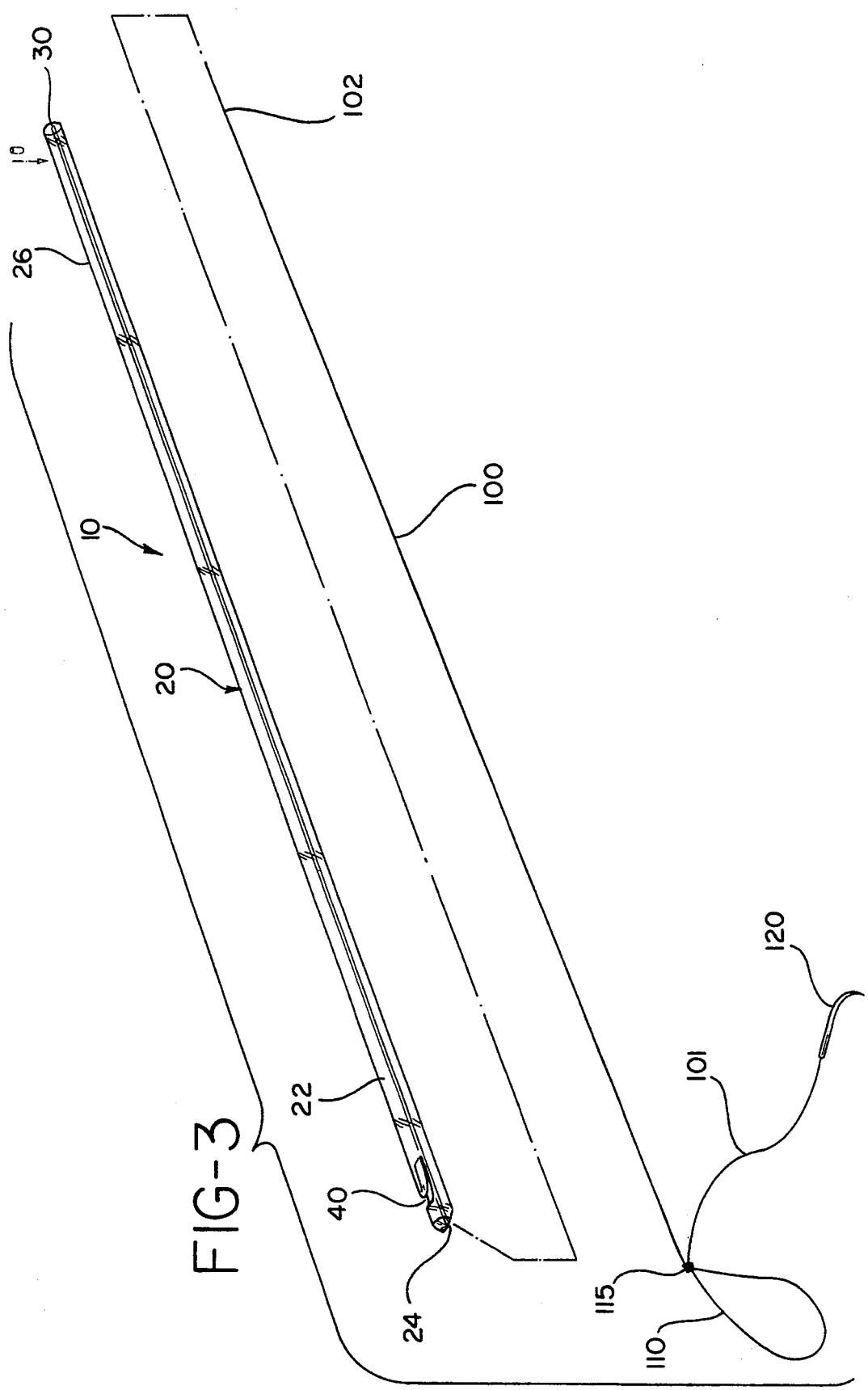

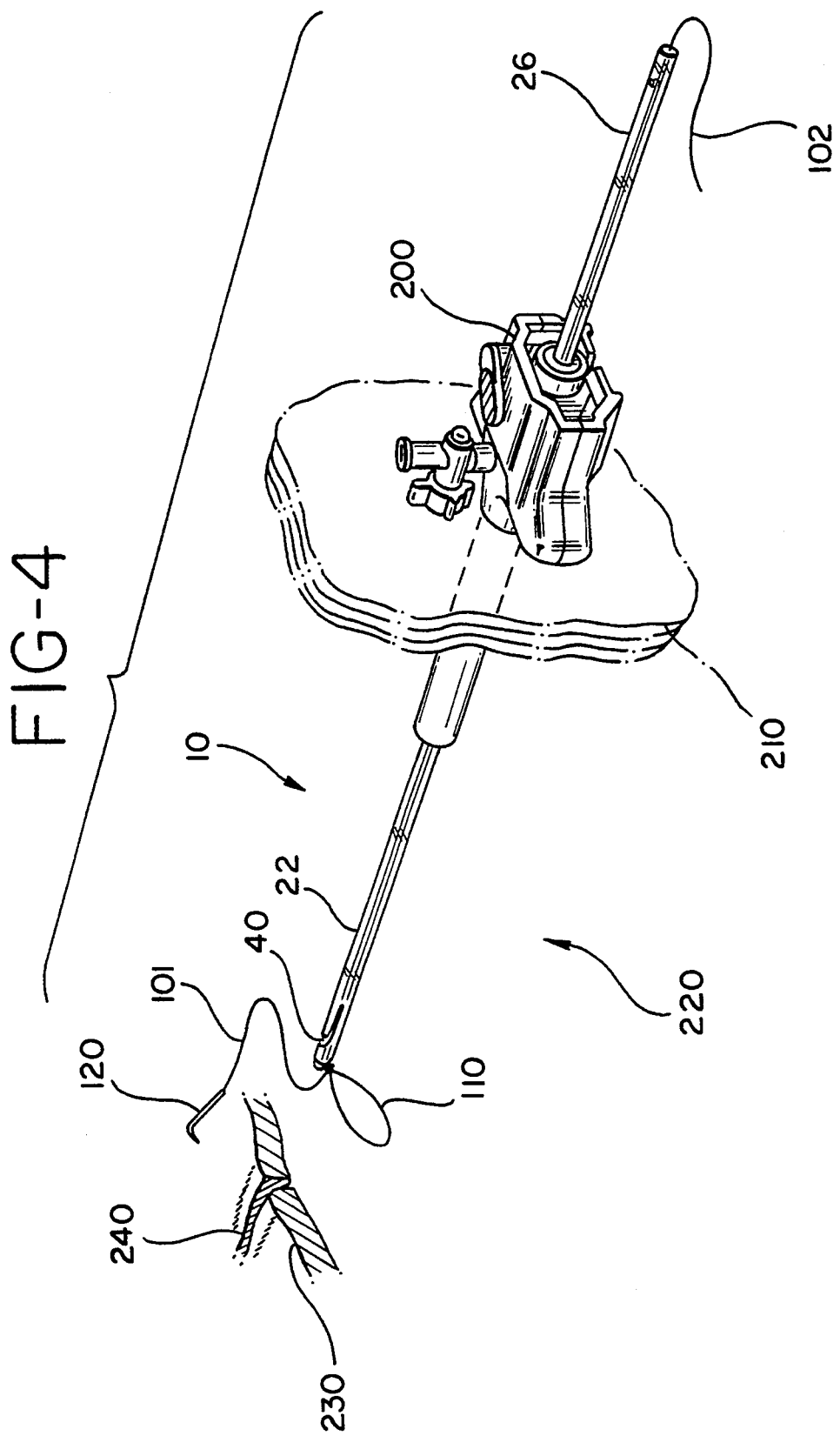

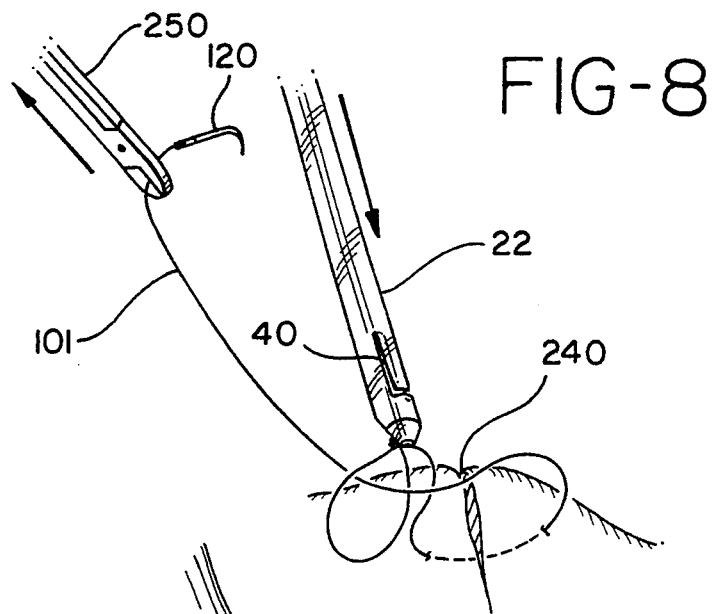
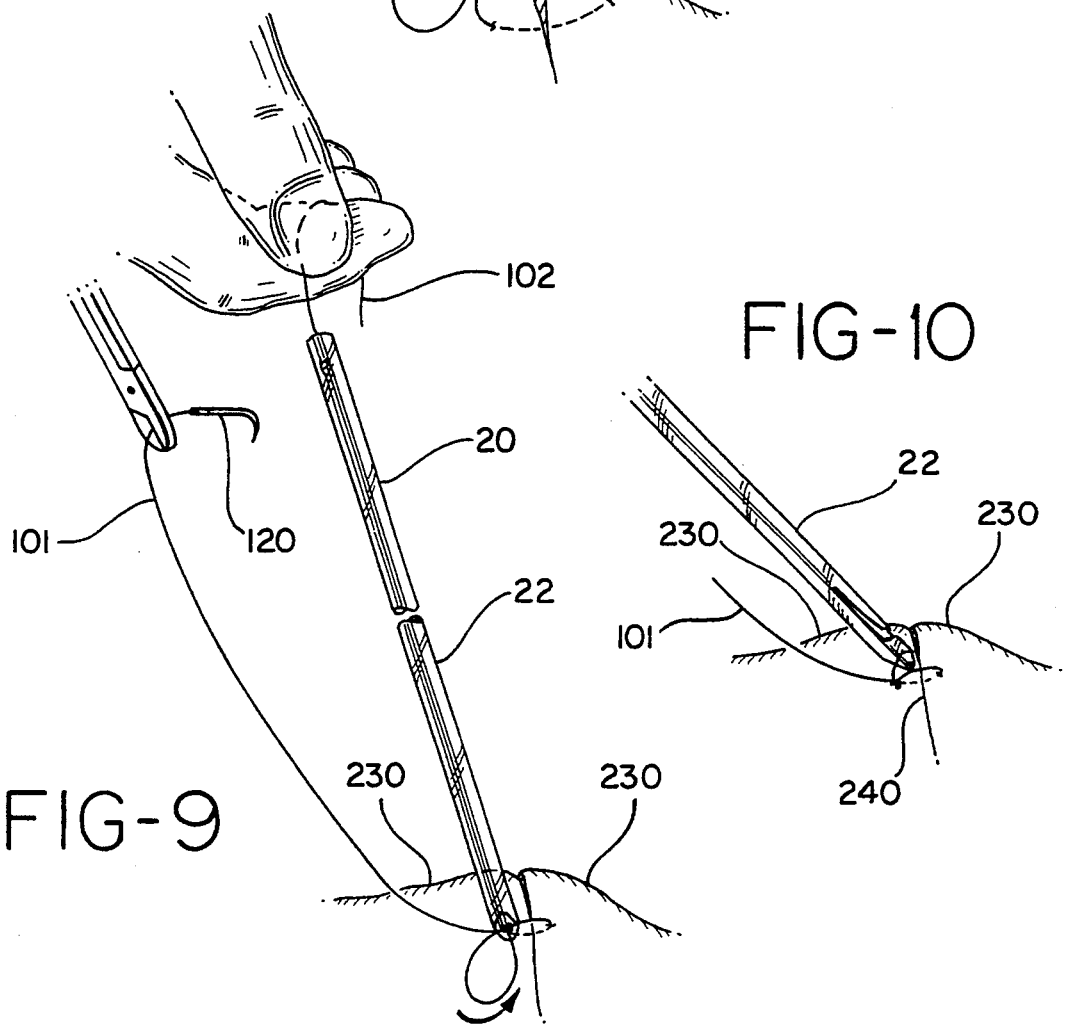

DEVICE FOR TYING INTRACORPOREAL KNOT

TECHNICAL FIELD

The field of art to which this invention relates is surgical instruments, in particular, surgical instruments used with surgical suture for tying knots.

BACKGROUND OF THE INVENTION

Endoscopic surgical ("endosurgical") procedures are becoming widely accepted Within the medical community and by the patient population. Endosurgical procedures, which include arthroscopy, laparoscopy, thoracoscopy and endoscopy, have been shown to have many benefits. The benefits include reduced post-operative recovery time, reduced stay in the hospital, reduced pain and reduced scarring.

Numerous endosurgical instruments have been developed to assist the surgeon in performing endoscopic procedures. The instruments include trocars and trocar cannulas, ligating clip appliers, stapling devices, graspers, endoscopic pouches, and the like. In addition, endoscopic suturing devices have been developed which assist the surgeon in suturing within a body cavity.

In most endosurgical procedures, trocars are inserted into a body cavity in order to give the surgeon access to the body cavity. Conventional trocars typically consist of an elongated piercing obturator concentrically housed within a trocar cannula. Trocar cannulas typically consist of an elongated tube mounted in a hollow handle. After the trocar is inserted into the body cavity, and positioned properly, the surgeon removes the trocar obturator thereby leaving the trocar cannula as a passage to the body cavity. Several trocar cannulas are typically employed in an endoscopic procedure. An endoscope is inserted through one of the trocar cannulas so that the surgeon can observe the interior of the body cavity. The remaining trocar cannulas are used for inserting various endosurgical instruments.

It can be appreciated that suturing during an endoscopic procedure presents challenges to both the surgeon and the equipment manufacturer. Various endoscopic surgical devices have been developed which allow the surgeon to suture remotely in a patient's body cavity. For example, endoscopic loop suturing devices have been developed. The loop suture devices consist of a pretied loop mounted to a cannula. Other endoscopic suturing devices have been developed such as pre-tied knots mounted to cannulas, Although the endosurgical suturing devices which have been developed are suitable for their intended purposes, there is a continuing need in the rapidly progressing endoscopic surgical arts for new instruments useful in endoscopic suturing.

DISCLOSURE OF THE INVENTION

Therefore, it is an object of the present invention to provide a suturing device which assists the surgeon in tying a knot during an endoscopic procedure.

It is a further object of the present invention to provide a device for tying an intracorporeal knot which is inexpensive to manufacture.

Accordingly, a device for tying an intracorporeal knot is disclosed. The device has a cannula tube. The cannula tube has a proximal end and a distal end. The tube has a longitudinal passage therethrough. A slit in the distal end of the tube extends proximally and axially a sufficient distance to effectively retain a suture.

Another aspect of the present invention is a combination of the above-described intracorporeal knot tying device and a surgical suture.

Yet another aspect of the present invention is an intracorporeal knot tying device. The knot tying device consists of a cannula having a proximal end and a distal end. The cannula tube has a longitudinal passage therethrough. The cannula has an arm for manipulating sutures which extends distally and axially from the distal end of the cannula and is separate from the outer surface of the distal end of the cannula by a space. The arm has a first member extending radially out from the outer surface of the cannula. The first member has an outer end. A second member extends distally from the outer end of the first member. The first member and the second member form the arm structure which is used to capture and manipulate suture in the space between the second member and the outer surface of the distal end of the cannula.

Still yet another aspect of the present invention is the combination of the above-described intracorporeal knot tying device having an arm-like member and a suture.

Yet a further aspect of the present invention is a method of tying a suture using either of the above-described intracorporeal knot tying devices.

Other features and advantages of the invention will be more apparent from the following description and accompanying drawings.

DESCRIPTION OF THE DRAWINGS

FIG. 1 is a perspective view of the intracorporeal knot tying device of the present invention loaded with an armed suture.

FIG. 2 is partial cross sectional view of the distal end of the intracorporeal knot tying device of FIG. 1.

FIG. 3 is an exploded perspective view of the intracorporeal knot tying device of FIG. 1.

FIG. 4 is a perspective view of the intracorporeal knot tying device of the present invention inserted through a trocar cannula which has been inserted through a body wall into the abdominal cavity of a patient.

FIG. 8 illustrates the distal end of the suture after it has been pulled through the suture loop, while the cannula is advanced until the end of the cannula and the suture loop rest upon the tissue adjacent to the incision site.

FIG. 9 illustrates the base of the loop resting on the tissue along with the distal end of the cannula while tension is maintained on the needle end of the suture as the proximal end of the suture is pulled and the loop is tightened.

FIG. 10 illustrates the loop tightened about the suture.

THE BEST MODE FOR CARRYING OUT THE INVENTION

Figure 5:
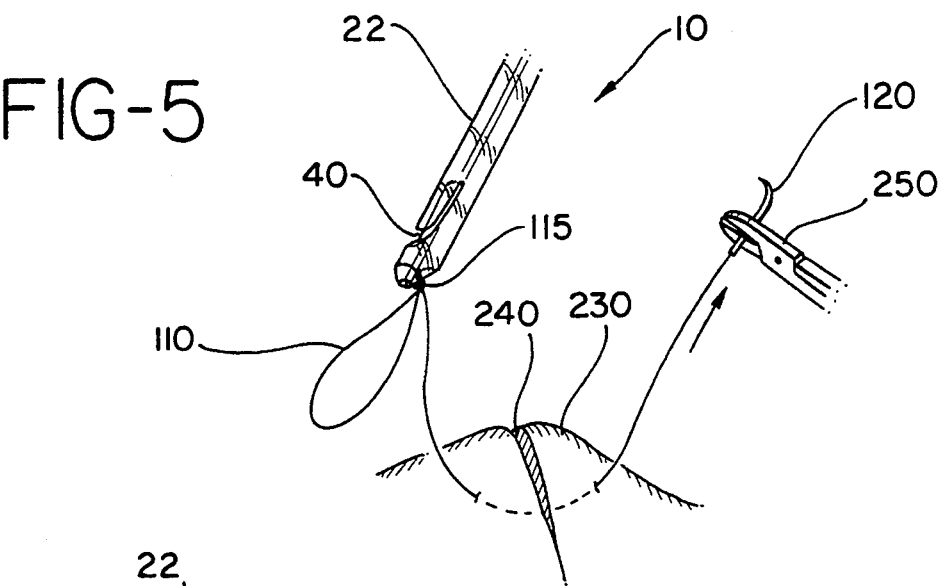
FIG. 5 illustrates a needle and suture being pulled through tissue surrounding both sides of an incision site.

The disclosure of U.S. Pat. No. 5,234,445 is incorporated herein in its entirety.

Referring to FIG. 1, an intracorporeal device 10 of the present invention is seen. The device 10 is seen to have cannula 20 having distal end 22 with tapered distal tip 24, and proximal end 26. The cannula 20 is seen to have axial, longitudinal passage 30. Optional angulated passage 35 is seen to be in communication with longitudinal passage 30. Located in the distal end 22 of cannula 20 is the suture retaining slot 40. The suture retaining slot 40 is seen to extend radially inward and distally sufficiently to form an effective slot for capturing and retaining a suture 100. Suture 100 is seen to be a conventional suture having a distal end 101 and a proximal end 102. Suture 100 is also seen to have distal suture loop 110 and slide knot 115 adjacent to loop 110. The intracorporeal knot tying device 10 is seen to have suture 100 which is threaded through the interior passages 30 and 35 of the cannula 20 such that the knot 115 and loop 110 are adjacent to distal tip 24 of cannula 20. Attached to the distal end 101 of suture 100 is the surgical needle 120. The suture is seen to have suture loop 110 formed therein and slip knot 115.

The surgical suture 100 can be any conventional surgical suture including absorbable, nonabsorbable, monofilament, multifilament, braided, etc. Examples of conventional absorbable sutures 100 which can be used with the intracorporeal knot tying devices 10 of the present invention include gut, polydiaxanone, polyglactin 910, and the like. Examples of non-absorbable sutures which can be used with the intracorporeal knot tying device of the present invention include silk, polyester, nylon, polypropylene and the like. The surgical needles 120 which can be used with the sutures 100 of the present invention include conventional surgical needles having taper points or cutting points. The needles 100 may be straight, curved, or may have straight and curved sections. The needles 100 are mounted to the sutures 100 using conventional attachment techniques.

Figure 17:
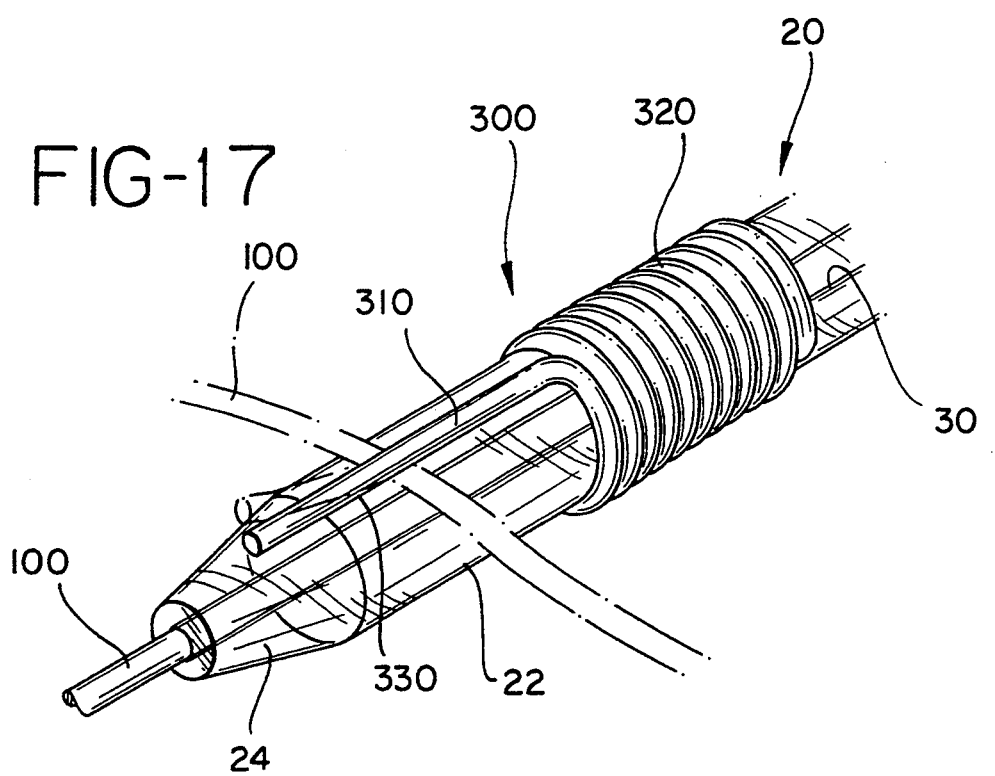
FIG. 17 illustrates an alternate embodiment of the intracorporeal knot tier of the present invention wherein a spring having a distal extension is used in place of the notch in the cannula.

An alternate embodiment of the knot tying device of the present invention is seen in FIG. 17. In that embodiment, the slot 40 is replaced by the member 300. Arm 310 of member 300 is seen to extend distally from helical spring member 320 which is mounted to the distal end 22 of cannula 20. The slot 330 is seen to be contained between the arm 310 and the distal end 22 of the cannula 20. A suture 100 is captured in slot 330 for manipulating during knot tying. The cannula 20 seen in FIG. 17 does not have optional angulated passage 35.

Figure 18:
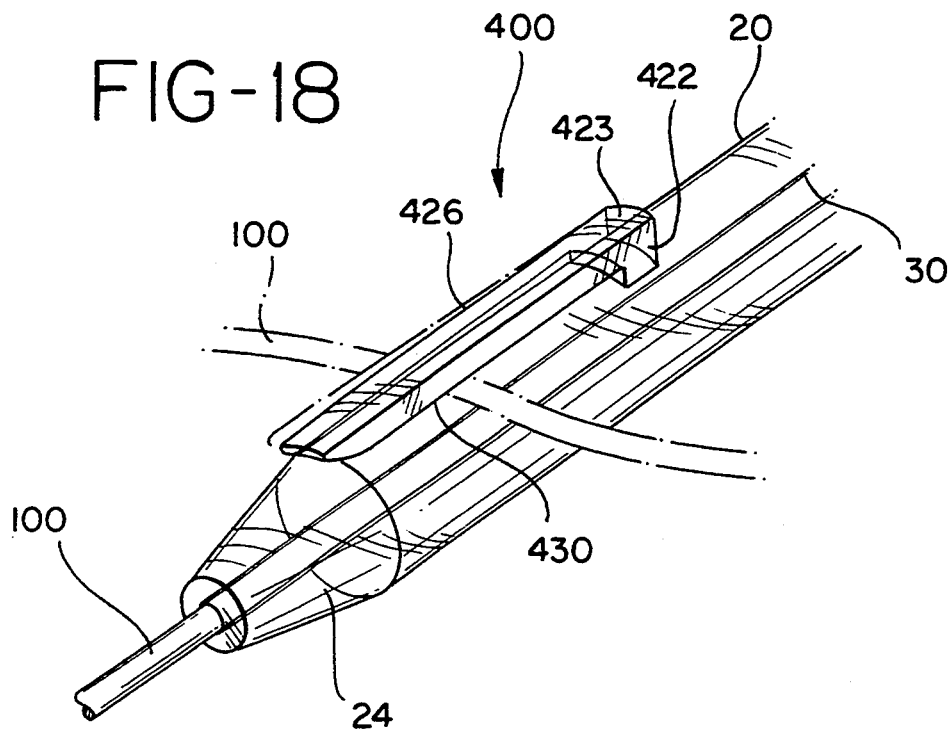
FIG. 18 illustrates an alternate embodiment of the present invention having a distally extending arm mounted to the distal end of the cannula in place of the slot in the cannula.

Yet another embodiment of the intracorporeal knot tying device 10 is seen in FIG. 18. In that embodiment, the slot 40 is replaced by the arm 400. Arm 400 is seen to have radial outwardly extending arm 422 mounted to the distal end of cannula 20. Extending from the end 423 of arm 422 is the distal member 426. The slot 430 is seen to be contained between the arm 420 and the proximal end 22 of the cannula 20. A suture 100 is captured in slot 430 for manipulating during knot tying.

Figure 6:
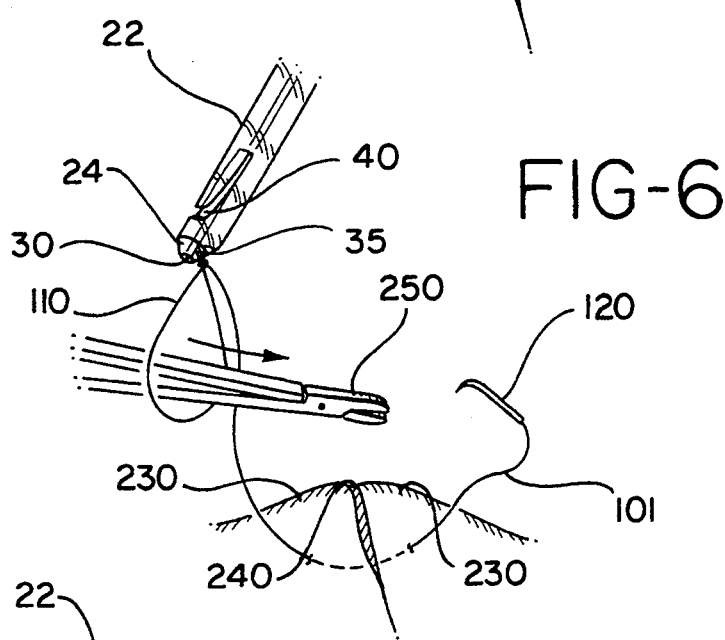
FIG. 6 illustrates a needle grasper being passed through the suture loop.
Figure 7:
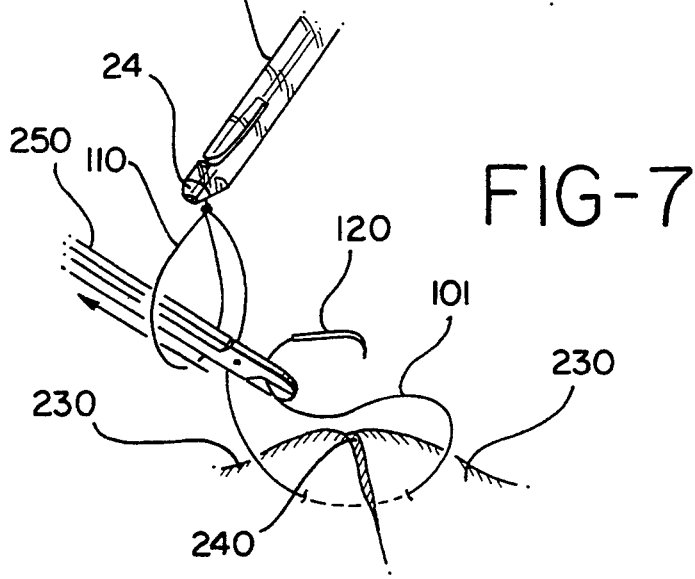
FIG. 7 illustrates the needle grasper grasping the suture just behind the surgical needle prior to pulling it through the suture loop.
Figure 11:
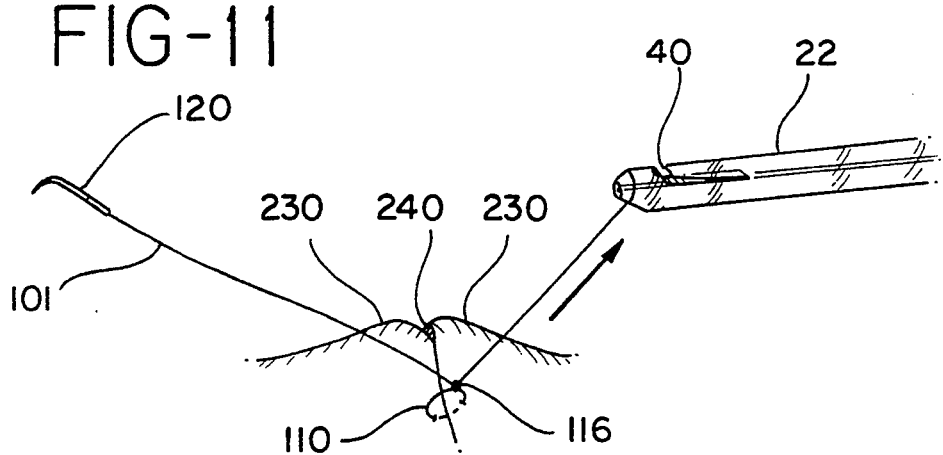
FIG. 11 illustrates the cannula moved to a proximal position with respect to the suture loop and incision.
Figure 12:
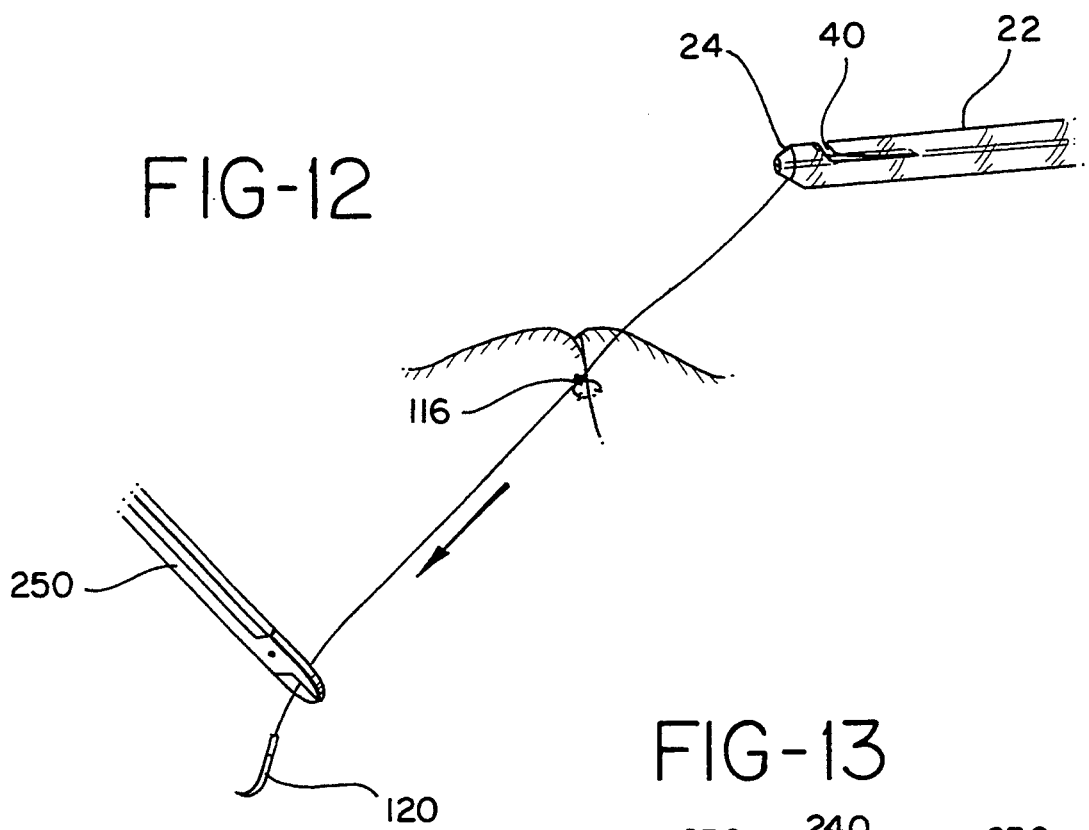
FIG. 12 illustrates the suture grasper grasping the needle end of the suture and placing tension upon it.
Figure 13:
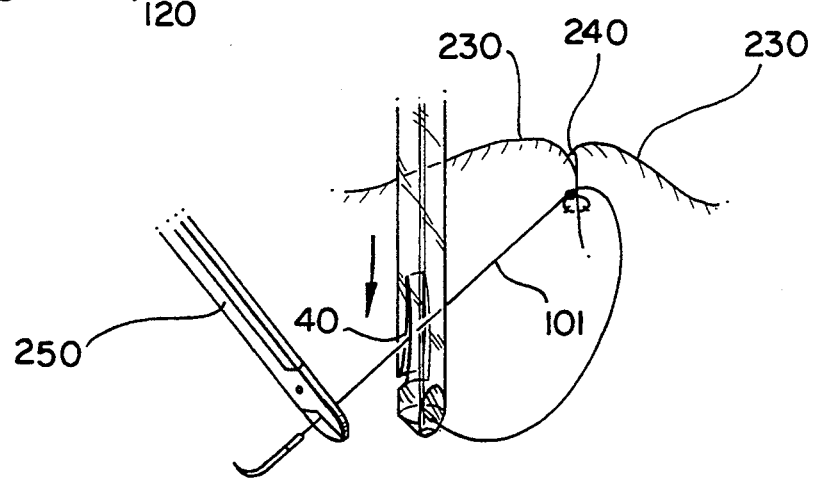
FIG. 13 illustrates the positioning of the cannula such that the distal end of the suture is contained within the notch on the cannula.
Figure 14:
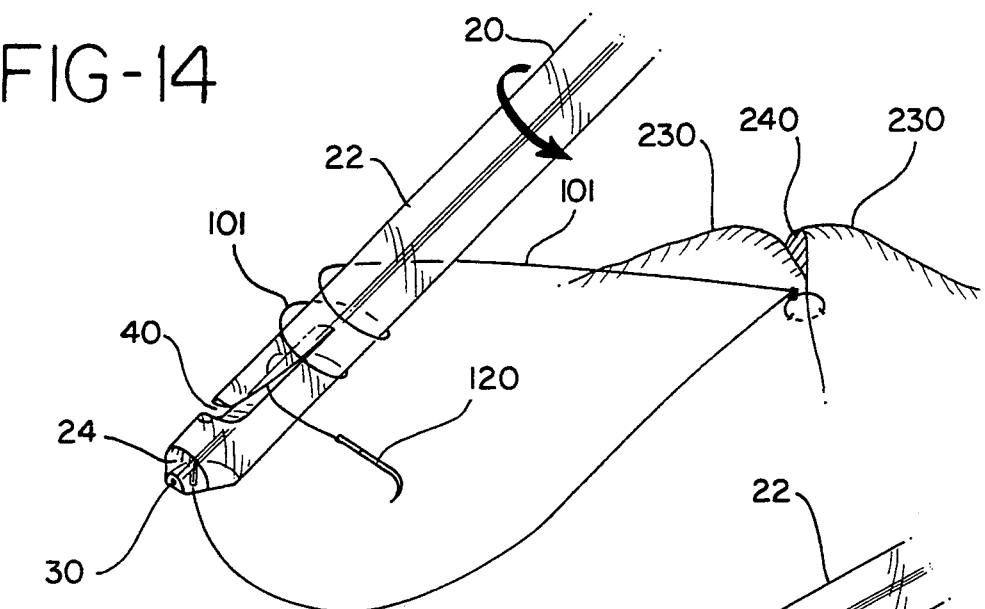
FIG. 14 illustrates the suture released from the needle grasper and the cannula after it has been rotated one to two times, thereby winding the needle end of the suture around the cannula.
Figure 15:
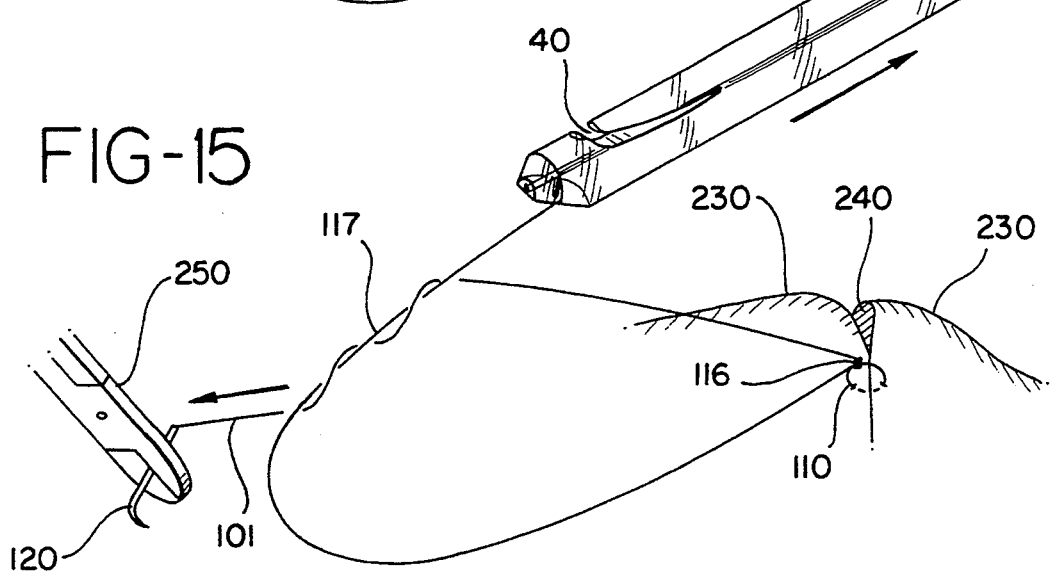
FIG. 15 illustrates the surgeon regrasping the surgical needle and pulling on the needle and the cannula, thereby causing the knot to slide off of the cannula (a simple throw or surgeons throw knot).
Figure 16:
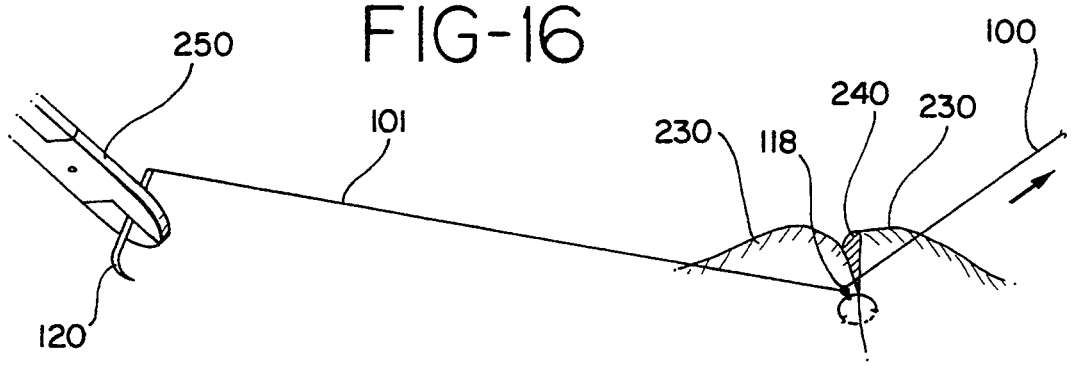
FIG. 16 illustrates the knot secured adjacent to the previously-tied knot at the incision.

The intracorporeal knot tying device 10 of the present invention is used in the following manner as illustrated in FIGS. 4–16. An intracorporeal knot tying device having a suture 100, suture loop 110, knot 115 and a needle 120 is inserted through a conventional trocar cannula 200 through a body wall 210 and into a body cavity 220 by inserting the distal end 22 of the cannula 20 and distal section of suture 100 with loop 110 and the needle 120 through the trocar cannula 200. The distal end 22 of the cannula and the suture 100 and needle 120 are maneuvered to the tissue site 230 where it is desired to suture incision 240. Referring to FIG. 5, the surgeon then grasps the surgical needle 120 with a conventional endoscopic needle grasper 250 and pushes the needle 120 through the tissue 230 about incision site 240. The surgeon then pulls the needle 120 along with the suture 100 through the tissue 230. Next, a knot 116 is formed in the suture 100. Referring to FIGS. 6 and 7, after the needle 120 has been passed through the two layers of tissue 230 about incision 240 (which are to be approximated), it is then grasped and passed through the pre-tied suture loop 110. Tension is applied on the needle or distal end 101 of the suture 100 so that the two layers of tissue 230 about incision 240 are pulled together. Next, as seen in FIGS. 8 and 9, the distal end of cannula 20 along with loop 110 are placed upon tissue site 230 adjacent to incision 240. The loop 110 is then cinched down by pulling on the slide or proximal end 102 of the suture 100 which is attached to the proximal end 26 of the cannula 20 which is located outside of the patient's body. Once the loop 110 has been tightened completely as seen in FIG. 10, the cannula 20 is backed off in the proximal direction to expose a sufficient amount of suture 110 inside the body cavity 220 effective for tying a knot, preferably about 2 to about 3 inches (see FIG. 11). The distal or needle end 101 of the suture then has a slight tension applied as it is pulled away from the incision site 240 and cannula 20 (see FIG. 12). Referring now to FIG. 13, the notch 40 in the cannula 20 is then placed about the distal or needle end 101 of the suture 100 that is attached to the needle 120. The notch 40 is placed close to the shaft of the needle 120 and the suture 100 is pushed sufficiently deep into the notch 40 until it is effectively secure. The needle 120 is then released from the grasper 250. Alternately, the needle 120 can be placed in the notch 40 also, and secured by pushing it sufficiently deep into the notch 40 to effectively retain the needle 120. The cannula 20, as seen in FIG. 14, is then twirled or twisted so that the distal end 101 of the suture 100 wraps around the distal end 22 of cannula 20 it at least two revolutions. As seen in FIG. 15, The needle 120 is re-grasped and tension is again applied to suture 100 in a direction away from the incision site 240. When this occurs the suture 100 is released out from the notch 40 and the suture 110 section which has been wrapped around the cannula 20 slips off in the distal direction forming a simple throw 117 as seen in FIG. 15. Referring to FIG. 16, by pulling on both the needle or distal end 101 of the suture 100 and the proximal end 102 of the suture 100, which is outside the body, the throw 117 can be tightened to form knot 118. Additional throws 117 can be added in the same manner. To form a square knot using the device 10, two throws are made with the second being formed by twisting the cannula 20 in the opposite direction from the first direction. In this instance, the first throw is not tightened completely. After the second throw is made, then the knot is securely tightened. By twisting the distal or needle end 101 of suture 100 around the distal end 22 of cannula 20 for three revolutions a surgeon's knot can be made.

If desired, the device 10 may be used in a similar manner to form intracorporeal knots using a suture 100 which does not have a pretied distal loop such as distal loop 110. The procedure would then be modified by one skilled in the art to accommodate the absence of the suture loop.

The following example is illustrative of the principals and practice of the present invention.

EXAMPLE 1

A patient was prepared for surgery using conventional surgical preparatory techniques. The patient was anesthetized with a sufficient dose of a conventional anesthesia to induce an effective anesthetized state. The patient's airway was cannulated witch a conventional endotracheal tube and the patient was hooked up to a conventional ventilator. Using conventional endosurgical techniques, four conventional trocars were inserted into the patient's abdominal cavity. The trocar obturators were then removed leaving the trocar cannulas as pathways to the body cavity. A conventional endoscope was inserted into one trocar cannula. The other trocar cannulas were utilized for the passage of various endosurgical instruments. The intracorporeal knot tying device 10 of the present invention was used in the following manner as illustrated in FIGS. 4-16. An intracorporeal knot tying device 10, having a suture 100, suture loop 110, knot 115 and a needle 120, was inserted through one of the conventional trocar cannulas 200 through the patient's body wall 210 and into the body cavity 220 by inserting the distal end 22 of the cannula 20 and distal section 101 of suture 100 with loop 110 and the needle 120 through the trocar cannula 200. The distal end 22 of the cannula and the suture 100 and needle 120 were maneuvered to the tissue site 230 where it was desired to suture incision 240. Referring to FIG. 5, the surgeon then grasped the surgical needle 120 with a conventional endoscopic needle grasper 250 and pushed the needle 120 through the tissue 230 about incision site 240. The surgeon then pulled the needle 120 along with the suture 100 through the tissue 230. Next, a knot 116 was formed in the suture 100. Referring to FIGS. 6 and 7, after the needle 120 had been passed through the two layers of tissue 230 about incision 240 (which were to be approximated), it was then grasped and passed through the pre-tied suture loop 110. Tension was applied on the needle or distal end 101 of the suture 100 so that the two layers of tissue 230 about incision 240 were pulled together. Next, as seen in FIGS. 8 and 9, the distal end of cannula 20 along with loop 110 were placed upon tissue site 230 adjacent to incision 240. The loop 110 was then cinched down by pulling on the slide or proximal end 102 of the suture 100 which protrudes from the proximal end 26 of the cannula 20 which was located outside of the patient's body. Once the loop 110 had been tightened completely as seen in FIG. 10, the cannula 20 was backed off in the proximal direction to expose a sufficient amount of suture 110 inside the body cavity 220 effective for tying a knot, preferably about 2 inches (see FIG. 11). The distal or needle end 101 of the suture then had a slight tension applied as it was pulled away from the incision site 240 and cannula 20 (see FIG. 12). Referring now to FIG. 13, the notch 40 in the cannula 20 was then placed about the distal or suture end 101 of the suture 100 that was attached to the needle 120. The notch 40 was placed close to the shaft of the needle 120 and the suture 100 was pushed sufficiently deep into the notch 40 until it was effectively secure. The needle 12 was then released from the grasper 250. The cannula 20, as seen in FIG. 14, was then twirled or twisted so that the needle or distal end 101 of the suture 100 wrapped around the distal end 22 of cannula 20 for at least about two revolutions.

As seen in FIG. 15, the needle 120 was re-grasped and tension was again applied to suture 100 in a direction away from the incision site 240. When this occurred the suture 100 was released out from the notch 40 and the suture 110 section which had been wrapped around the cannula 20 slipped off in the distal direction forming a simple throw 117 as seen in FIG. 15. By pulling on both the needle or distal end 101 of the suture 100 and the proximal end 102 of the suture 100, which was outside the body, the throw 117 can be tightened to form knot 118 as seen in FIG. 16.

The intracorporeal knot tying device of the present invention has many advantages including that knots may be tied by easily twisting a cannula; that different types of knots may be tied; that the techniques to tie different knots are all very similar; that a variety of knot tying devices can be adapted to include this concept; that a multitude of knots can be tied, one on top of the next, for added security; that the device does not have to be removed out of the trocar cannula to tie additional knots; and that there are no moving parts or mechanisms which need to be operated.

Although this invention has been shown and described with respect to detailed embodiments thereof, it will be understood by those skilled in the art that various changes in form and detail thereof may be made without departing from the spirit and scope of the claimed invention.

What is claimed is:

1. An intracorporeal knot tying device, comprising:
a cannula tube, the tube having a proximal end and a distal end, the tube further having a longitudinal passage therethrough;and,
a slit in the distal end of the tube extending proximally and radially inward a sufficient distance to effectively retain a suture.

2. The device of claim 1 wherein the cannula tube additionally comprises a distal tapered end.

3. The device of claim 1 further comprising a suture mounted in the passage, the suture having a distal end and a proximal end, wherein the distal end of the suture extends through the passage beyond the distal end of the cannula.

4. The device of claim 3 further comprising a surgical needle mounted to the distal end of the suture.

5. The device of claim 3 further comprising a loop means in the distal end of the suture.

6. The device of claim 5 further comprising a surgical needle mounted to the distal end of the suture.

7. An intracorporeal knot tying device, comprising:
a cannula tube, the tube having a proximal end and a distal end, the tube further having a longitudinal passage therethrough, a longitudinal axis, and an inner surface and an outer surface; and
means mounted to the distal end of the cannula for engaging a suture, wherein the suture engaging means comprises a first arm member extending radially outward from the outer surface of the distal end of the cannula, said member having an outer end, and a second arm member extending distally from the outer end of the first member, substantially parallel to the longitudinal axis of the cannula, such that there is a space between the second arm member and the outer surface of the distal end of the cannula effective to retain a suture.

8. The device of claim 7 wherein the cannula tube additionally comprises a distal tapered end.

9. The device of claim 7 further comprising a suture mounted in the passage, the suture having a distal end and a proximal end wherein the distal end of the suture extends through the passage beyond the distal end of the cannula.

10. The device of claim 9 further comprising a surgical needle mounted to the distal end of the suture.

11. The suture of claim 9 further comprising a loop means in the distal end of the suture.

12. The device of claim 11 further comprising a surgical needle mounted to the distal end of the suture.

13. The combination comprising:
an intracorporeal knot tying device, wherein the device comprises,
a cannula tube, having a proximal end and a distal end, the tube having a longitudinal passage therethrough,
and a slit in the distal end of the tube extending proximally and radially inward a sufficient distance to effectively retain a suture; and,
a suture.

14. The combination comprising:
an intracorporeal knot tying device, comprising
a cannula tube, the tube having a proximal end and a distal end, the tube further having a longitudinal passage therethrough, a longitudinal axis, and an inner surface and an outer surface, and means mounted to the distal end of the cannula for engaging a suture, wherein the suture engaging means comprises a first arm member extending radially outward from the outer surface of the distal end of the cannula, said member having an outer end, and a second arm member extending distally from the outer end of the first member, substantially parallel to the longitudinal axis of the cannula, such that there is a space between the second arm member and the outer surface of the distal end of the cannula effective to retain a suture; and,
a surgical suture.

15. A method of tying an intracorporeal knot comprising the steps of:
inserting a cannula, said cannula comprising a proximal end and a distal end and a longitudinal axis, into a body cavity, said cannula further comprising means for engaging a suture mounted to the distal end thereof and a longitudinal passage therethrough, said cannula additionally comprising a suture mounted in said longitudinal passage, said suture having a distal end extending from the distal end of the cannula, such that at least the distal end of the cannula is in said body cavity, wherein the suture engaging means comprises a cylindrical member having a proximal and a distal end, said cylindrical member comprising a plurality of adjacent connected coils and a distal arm member extending distally from the distal end of the cylindrical member;
engaging a section of the distal end of the suture in the suture engaging means;
rotating the cannula at least about two revolutions about its longitudinal axis to form at least about two loops of suture about the distal end of the cannula;
releasing the suture from the suture engaging means;
releasing the suture loops onto the suture; and,
forming a surgical knot in the suture.

* * * * *